(12) United States Patent
Gabbay

(10) Patent No.: US 6,783,556 B1
(45) Date of Patent: Aug. 31, 2004

(54) SYSTEM AND METHOD FOR MAKING A CALOTTE-SHAPED IMPLANTABLE SHEATH

(76) Inventor: Shlomo Gabbay, #1 Randall Dr., Short Hills, NJ (US) 07078

(*) Notice: Subject to any disclaimer, the term of this patent is extended or adjusted under 35 U.S.C. 154(b) by 255 days.

(21) Appl. No.: 09/669,821

(22) Filed: Sep. 26, 2000

(51) Int. Cl.[7] .................................................. A61F 2/54
(52) U.S. Cl. ...................................... 623/66; 623/23.72
(58) Field of Search .............................. 623/2, 99, 66; 530/356

(56) References Cited

U.S. PATENT DOCUMENTS

| | | | |
|---|---|---|---|
| 3,966,401 A | | 6/1976 | Hancock et al. |
| 4,268,131 A | * | 5/1981 | Miyata et al. ........... 351/160 H |
| 5,332,802 A | * | 7/1994 | Kelman et al. ............. 530/356 |
| 5,545,215 A | * | 8/1996 | Duran ........................ 623/1.26 |
| 6,293,971 B1 | * | 9/2001 | Nelson et al. ........... 623/23.62 |
| 6,352,708 B1 | * | 3/2002 | Duran et al. ................. 424/423 |
| 6,503,277 B2 | * | 1/2003 | Bonutti .................... 623/11.11 |

OTHER PUBLICATIONS

International Search Report for PCT/US0127159.

* cited by examiner

Primary Examiner—David J. Isabella
(74) Attorney, Agent, or Firm—Tarolli, Sundheim, Covell & Tummino L.L.P.

(57) ABSTRACT

A system and method are disclosed for making a calotte-shaped implantable sheath. A sheet of biological tissue is held against a curved tissue-engaging surface while a fixation solution is applied to at least a substantial portion of the tissue. As a result, at least a portion of the tissue is fixed to a shape that substantially conforms to the shape of the tissue-engaging surface.

8 Claims, 4 Drawing Sheets

SYSTEM AND METHOD FOR MAKING A CALOTTE-SHAPED IMPLANTABLE SHEATH

TECHNICAL FIELD

The present invention relates to implantable tissue and, more particularly to a system and method for making a calotte-shaped sheath of implantable tissue.

BACKGROUND

In various types of neurosurgery it is common to interpose a sheath of tissue between a patient's brain and skull for dural substitution, such as for use in neurosurgical procedures. Typically the sheath is actual dura mater from a human cadaver that has been appropriately treated. Alternatively, a sheath of biocompatible tissue may be used.

Because certain curved shapes are difficult to reproduce, a generally flat sheath of biocompatible tissue typically used. Therefore, a new approach is desirable that is able to produce curved implantable sheaths, such as generally semi-spherical (or calotte-shaped) sheaths.

SUMMARY

The present invention relates to system and method for making a calotte-shaped implantable sheath. A sheet of biological tissue, such as animal pericardium, is positioned onto a curved surface. A fixation solution is applied to a substantial portion of the tissue, as at least that portion is held generally flush against the curved surface. After the tissue has been appropriately fixed, peripheral portions of the sheath may be trimmed so as to form a calotte-shaped sheath of tissue suitable for implantation. The sheath conforms to the contour of the curved surface against which it was fixed. As a result, the sheath is able to conform to the shaped of a curved structure, such as an organ or brain, when implanted.

One aspect of the present invention provides a system for creating a calotte-shaped implantable sheath. The system includes a curved tissue-engaging surface and means for holding a sheet of biological tissue against the tissue-engaging surface during fixation. A volume of a fixation solution is operable to fix at least a substantial portion of the tissue substantially to the shape of the tissue-engaging surface.

Another aspect of the present invention provides a method for forming a calotte-shaped implantable sheath. A sheet of tissue is placed against a curved surface and fixed with a fixation solution while at least a substantial portion of the tissue is held against the curved surface so that at least that portion of the tissue conforms to the shape of the curved surface.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which.

DESCRIPTION OF THE INVENTION

Various illustrative aspects of the present invention will now be described in connection with FIGS. 1–7 in which like reference numbers refer to like elements throughout the various views.

The present invention provides a system and method that may be used to fix tissue to a desired shape so as to better conform to contoured organs and tissue against which the tissue is to engage when implanted. While the following examples will be described with respect to forming a calotte-shaped sheath of tissue, those skilled in the art will understand and appreciate that other shapes, such as cylindrical sheaths and curved arches, also may be formed in accordance with the present invention.

Figure 1:
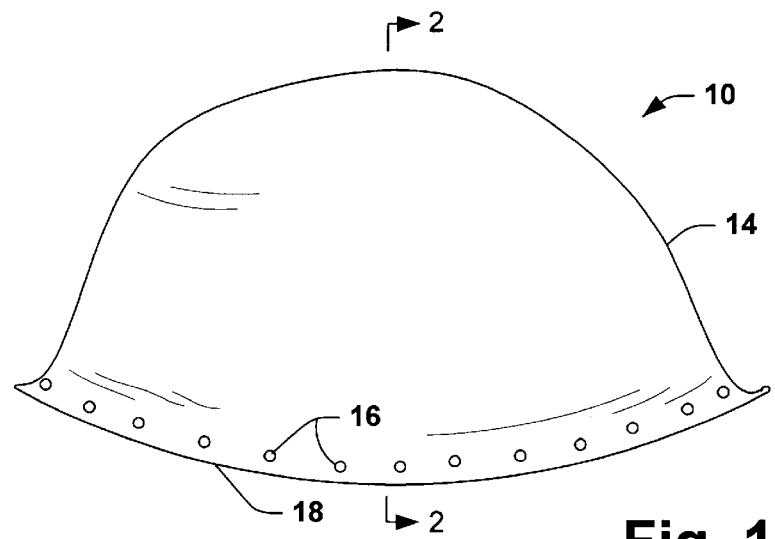
FIG. 1 is an example of a base member having a surface over which tissue may be fixed in accordance with the present invention.
Figure 2:
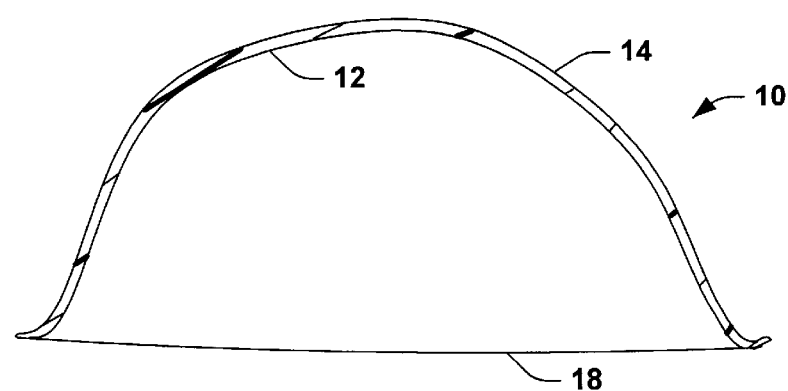
FIG. 2 is a cross-sectional view of the base member of FIG. 1 taken along line 2—2.

Turning now to FIGS. 1 and 2, a generally semi-spherical base 10 is illustrated. The base 10, which may be a bowl formed of a rigid material (e.g., a metal or plastic material), has an inner surface 12 and an outer surface 14. In this example, the inner surface 12 is curved in a convex manner and the outer surface 14 is curved in a generally concave manner.

In accordance with an aspect of the present invention, the inner and/or outer surfaces 12 and 14, respectively, may be dimensioned and configured to correspond to the shape of a selected part of a human brain. It is to be appreciated that other shapes and sizes may be utilized to process tissue to have a desired contour, such as for implantation in other types of surgical procedures. In addition, the inner surface 12 may be dimensioned to have radius of curvature that is less than the outer surface 14. The inner-and outer surfaces 12 and 14 also may have different shapes or contours. As a result, differently dimensioned and/or shaped sheaths may be formed with the same base 10.

Figure 3:
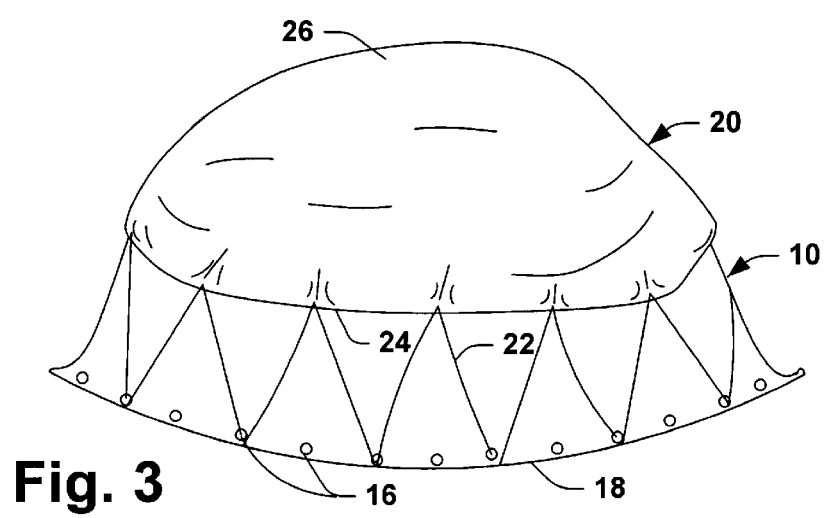
FIG. 3 is an example of tissue held against the surface of a base member in accordance with the present invention.

In this example, the base 10 also has a plurality of apertures 16 located near an open end 18 of the base. The apertures 16 provide a convenient way to secure a sheet of tissue 20 to the outer surface 14 of the base 10, such as shown in FIG. 3. The sheet of tissue 20 may be substantially any type of biological tissue. By way of example, the tissue may be animal pericardium (e.g., equine, bovine, porcine, etc.), collagen, animal dura mater, or other type of suitable sheet of tissue. To provide better results, the sheet of tissue should be a generally fresh, soft sheet of tissue. The sheet of tissue 20 may be in nearly any shape, such as rectangular, circular, elliptical, etc.

By way of illustration, one or more sutures 22 are sewn through a perimeter edge 24 of the tissue 20 so as to hold at least a substantial portion of the tissue in engagement with the outer surface 14 of the base 10. For the example when the tissue is animal pericardium, the smooth or visceral side of the pericardium should engage the outer surface 14 with the more rough side exposed. Typically at least a central part 26 of the tissue 20 is maintained in completely against the surface 14, and it is this part of the tissue that is used to form a calotte-shaped sheath in accordance with an aspect of the present invention.

While the example of FIG. 3 illustrates sutures being utilized to temporarily attach the tissue relative to the base 10, it is to be appreciated that other means also may be utilized to hold the tissue relative to the base in accordance with an aspect of the present invention. For example, suitable hooks or clamps could be employed to secure the tissue relative to the base 10 or other appropriate structure.

Figure 4:
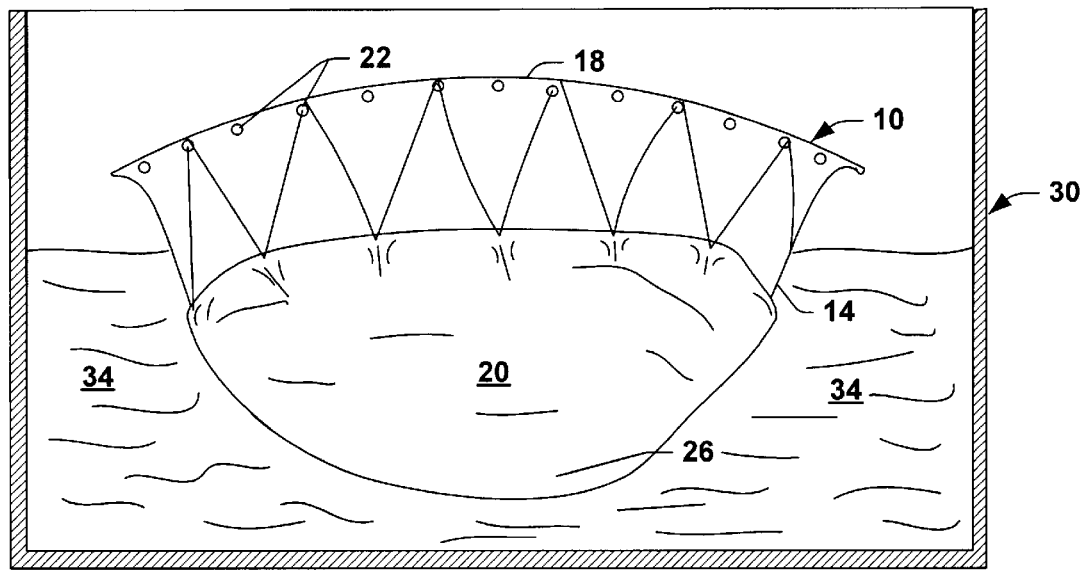
FIG. 4 is an example of tissue being fixed to a desired shape in accordance with the present invention.

FIG. 4. illustrates an example of a system 30 that may be employed to fix the tissue 20 to a desired shape in accordance with an aspect of the present invention. In this example, the system 30 includes a chamber 32 that contains a volume of a suitable fixation solution 34. The combination of the tissue 20 attached to the base 10 is emersed into the fixation solution 34 for sufficient period of time so as to fix the tissue that is exposed to the solution to substantially the same shape as the outer surface 14 of the base. By way of example, the fixation solution 34 is a solution that includes glutaraldehyde, which is well known in the art. A time period of about twenty-four hours in a glutaraldehyde solution should be sufficient to fix the tissue 20.

Figure 5:
FIG. 5 is an example of a calotte-shaped sheath produced from tissue treated in accordance with the present invention.

The tissue 20 may then be removed from the solution 34 and detached from the base 10. The tissue 20 is then trimmed to a desired size to form a calotte-shaped sheath 40, such as shown in FIG. 5. When the sheath 40 is to be used in neurosurgery as substitute dura mater, for example, the sheath may have diameter from about 10 cm to about 14 cm, although other sized sheaths also could be formed in accordance with an aspect of the present invention. The trimmed peripheral portion may be discarded or used to form other implantable tissue products. After initial fixation and trimming, the calotte-shaped sheath 40 may be placed back in a suitable solution, such as may contain glutaraldehyde, for additional curing. In particular, the natural tissue sheath 40 further may be cross-linked with glutaraldehyde and undergo a detoxification process with heparin bonding, such as according to the NO-REACT® treatment process from Shelhigh, Inc. of Millburn, New Jersey. The NO-REACT® tissue treatment process helps improve the biocompatibility of the sheath 40.

Figure 6:
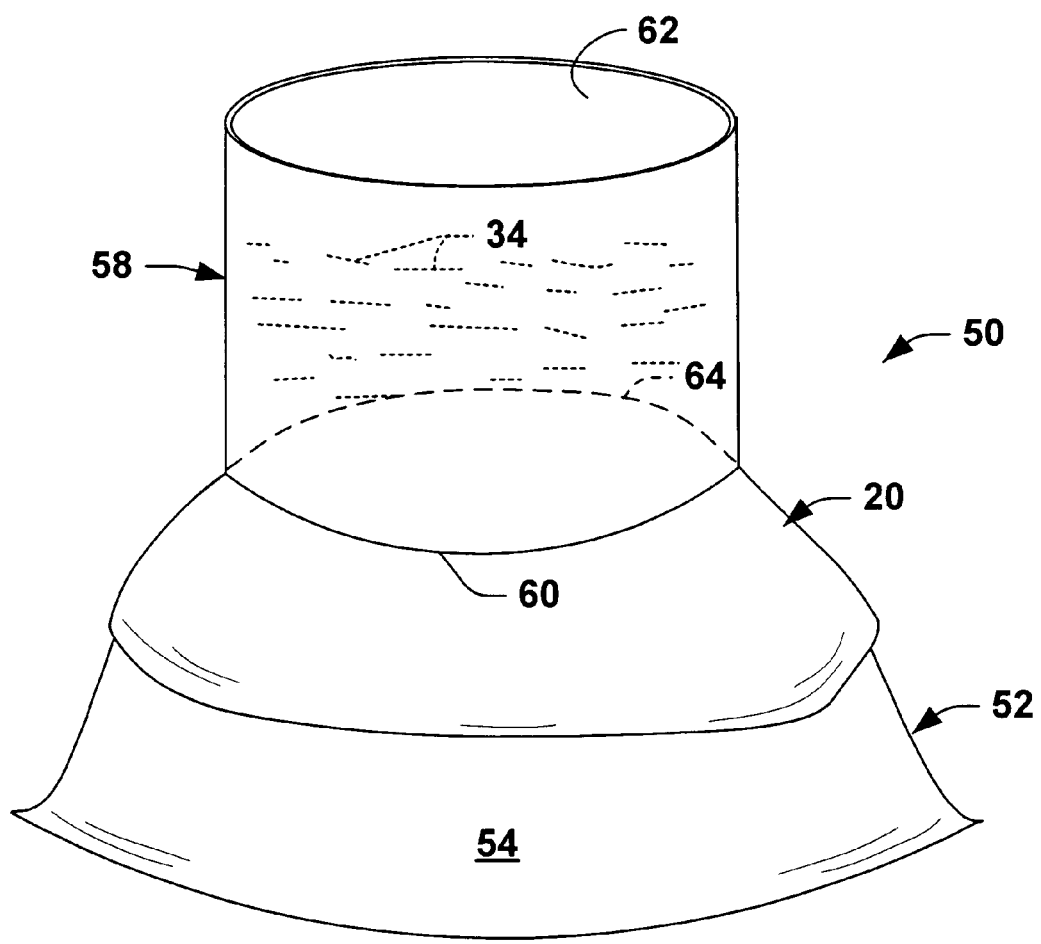
FIG. 6 is another example of tissue being fixed to a desired shape in accordance with the present invention.

FIG. 6 illustrates another system 50, in accordance with an aspect of the present invention, which may be employed to form an implantable calotte-shaped sheath 40. The system 50 includes a base 52 having a curved, generally semispherical (e.g. convex) outer surface 54. For example, the base 52 may be hollow bowl, although any structure having a desired outer surface 54 could be used. A sheet of biological tissue 20 is placed onto the outer surface 54 of the base 52, as shown in FIG. 6.

In contrast to the sutures and apertures utilized in the system of FIGS. 3 and 4, a generally tubular apparatus 58, such as a hollow cylinder, is used to hold the tissue 20 in a desired position relative to the base 52. In particular, the tubular apparatus 58 has a tissue-engaging end 60 that engages the tissue 20 and sandwiches the tissue between the outer surface 54 and the end 60. The engagement between the tissue-engaging end 60 and the tissue 20 may form a substantially liquid tight seal. In order to improve the seal, a rubber or other soft material may be provided at the end 60. As a result, an interior surface 62 of the tubular apparatus 58 and a portion 64 of the tissue 20 extending within the end 60 define a volume for holding a fixation solution 34. That is, the fixation solution 34 may be provided into the tubular apparatus 58 to fix the portion 64 of the tissue 20 within the annular end 60 to substantially the same shape as the outer surface contacted thereby. If some of the solution 34 leaks through the juncture between the tubular apparatus 58 and the tissue 20, the fluid simply would need to be replenished. Advantageously, the weight of the fixation solution 34 further helps to hold the central portion 64 of the tissue 20 against the outer surface 54 to promote a desired shape during fixation.

After fixing the tissue 20 for a suitable time period (e.g., about twenty-four hours), the tissue may then be removed from the system 50 and trimmed to form a calotte-shaped sheath 40, such as shown in FIG. 5.

While the apparatus 58 is shown and described as being generally cylindrical it is to be appreciated that other shapes also could be used in accordance with the present invention. Typically, however, the tissue-engaging end 60 of the apparatus should conform to the contour of the outer surface 54 and have a sufficient diameter so as to fix a desired portion 64 of the tissue 20.

Figure 7:
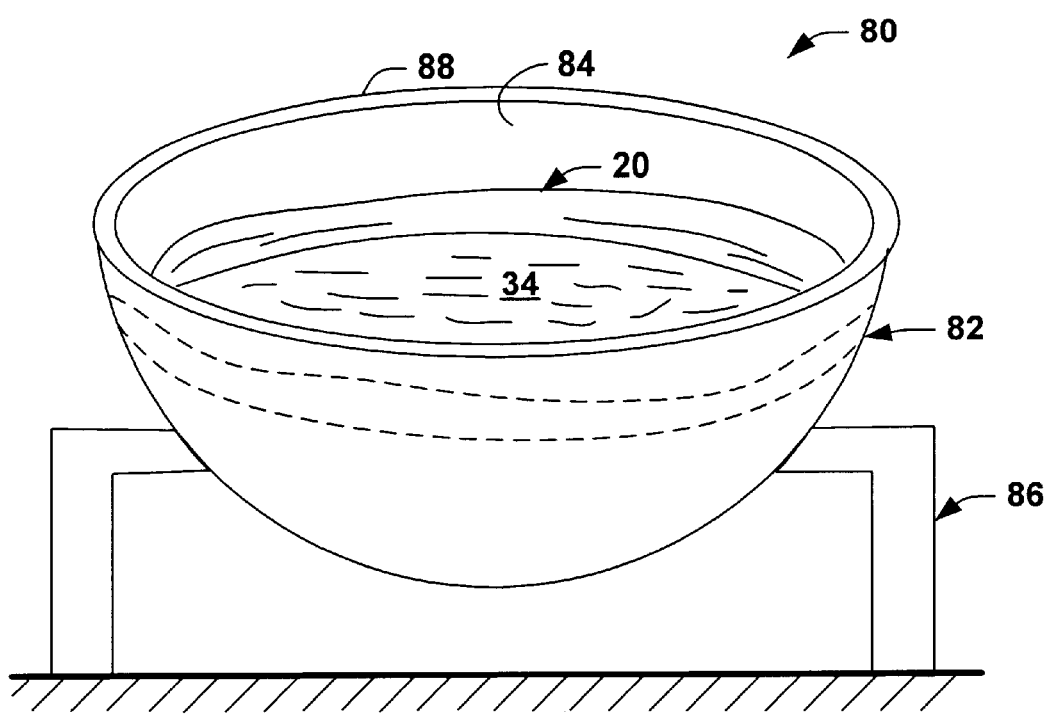
FIG. 7 is yet another example of tissue being fixed to a desired shape in accordance with the present invention.

FIG. 7 illustrates yet another example of a system 80 that may be utilized, in accordance with an aspect of the present invention, to form a calotte-shaped sheath 40 of tissue. The system 80 includes a base portion 82 having a convex inner surface 84. The base portion 82, for example, may be a bowl similar to the other system arrangements shown and described herein. An appropriate support apparatus 86 may be employed to hold the base portion 82 in a desired position, such that an open end 88 faces upwards. In this example, sheet of tissue 20 is placed against the inner surface 84 of the base. For the example where the tissue 20 is animal pericardium, the smooth side engages the inner surface 84. The tissue 20 may be smoothed out by hand (or by a suitable instrument) so that at least a substantial portion (e.g., a central portion) of the tissue 20 is substantially flush against the inner surface 84 the base 82.

After the tissue is at a desired position, a volume of a suitable fixation solution 34, such as may include glutaraldehyde, is added to a volume defined by the sheath 20 within the base 82. The weight of the fixation solution 34 helps maintain engagement between at least a substantial portion of the tissue 20 and the inner surface 84, thereby promoting fixation of the tissue to the desired shape. In order to facilitate engagement between the tissue 20 and the inner surface 84, a cup-shaped member, such as felt or other diffusable material, may be placed over the tissue within the base to help hold the tissue against the inner surface 84 of the base 82. After the tissue 20 has been fixed for a suitable time phase, the tissue may be removed and trimmed to a desired shape, such as to form the calotte-shaped sheath shown in FIG. 5.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" and variants thereof or the term "having" and variants thereof are used in either the detailed description or the claims, each such term is intended to be inclusive in a manner similar to the term "comprising."

What is claimed is:

1. A method for forming a calotte-shaped implantable sheath comprising the steps of:

placing a sheet of tissue against a curved surface, wherein the tissue has a perimeter portion;

applying at least one suture through the perimeter portion to hold the tissue against the curved surface during fixation;

fixing the tissue with a fixation solution while at least a substantial portion of the tissue is held against the curved surface so that the at least a substantial portion of the tissue conforms to the shape of the curved surface; and trimming a peripheral portion from the tissue to form the calotte-shaped implantable sheath.

2. The method of claim 1, wherein the curved surface is convex.

3. A method for forming a calotte-shaped implantable sheath comprising the steps of:

placing a sheet of tissue against a curved surface; and fixing the tissue with a fixation solution while at least a substantial portion of the tissue is held against the curved surface so that the at least a substantial portion of the tissue conforms to the shape of the curved surface; and using a generally annular end of a tubular apparatus to hold the tissue against the curved surface during fixation, wherein part of an interior surface of the tubular apparatus and a portion of the tissue extending within the annular end define a volume for holding the fixation solution.

4. A method for forming a calotte-shaped implantable sheath comprising the steps of:

placing a sheet of tissue against a concave surface;

fixing the tissue with a fixation solution while at least a substantial portion of the tissue is held against the concave surface so that the at least a substantial portion of the tissue conforms to the shape of the concave surface, wherein the solution helps to hold the tissue in engagement with the concave surface during fixation.

5. The method of claim 1, wherein the tissue is a sheet of animal pericardium.

6. The method of claim 5, wherein the sheet of animal pericardium has a smooth side that is positioned into engagement with curved surface during fixation.

7. The method of claim 1, wherein the curved surface is a semi-spherical surface.

8. A method for forming a calotte-shaped implantable sheath comprising the steps of:

placing a sheet of tissue against a curved surface;

applying at least one suture through a perimeter portion of the tissue to hold the tissue against the curved surface;

fixing the tissue with a fixation solution while at least a substantial portion of the tissue is held against the curved surface by the at least one suture so that the at least a substantial portion of the tissue conforms to the shape of the curved surface; and trimming the peripheral portion including the at least one suture from the tissue to form the calotte-shaped implantable sheath.

* * * * *